(12) United States Patent
Yun et al.

(10) Patent No.: US 10,970,842 B2
(45) Date of Patent: Apr. 6, 2021

(54) METHOD AND DEVICE FOR IDENTIFYING PATHOLOGICAL PICTURE

(71) Applicant: Sun Yat-sen University Cancer Center, Guanzhou (CN)

(72) Inventors: Jing-Ping Yun, Guanzhou (CN); Zhi Wang, Guanzhou (CN)

(73) Assignee: Sun Yat-sen University Cancer Center, Guanzhou (CN)

( * ) Notice: Subject to any disclaimer, the term of this patent is extended or adjusted under 35 U.S.C. 154(b) by 75 days.

(21) Appl. No.: 16/380,701

(22) Filed: Apr. 10, 2019

(65) Prior Publication Data
US 2019/0311479 A1    Oct. 10, 2019

(30) Foreign Application Priority Data
Apr. 10, 2018    (CN) .......................... 201810315279.0

(51) Int. Cl.
*G06K 9/00* (2006.01)
*G06T 7/00* (2017.01)
(Continued)

(52) U.S. Cl.
CPC .......... *G06T 7/0016* (2013.01); *G06K 9/6257* (2013.01); *G06N 3/08* (2013.01);
(Continued)

(58) Field of Classification Search
CPC .................................................. G06T 7/0016
See application file for complete search history.

(56) References Cited

U.S. PATENT DOCUMENTS

2017/0372471 A1    12/2017   Eurèn
2018/0165809 A1*   6/2018    Stanitsas ............... G06T 7/0012
(Continued)

FOREIGN PATENT DOCUMENTS

CN    107368670    11/2017
CN    107516317    12/2017
(Continued)

OTHER PUBLICATIONS

China National Intellectual Property Administration, "First Notification of Office Action," issued in connection with Chinese Application No. 201810315279.0 with English translation, dated Nov. 28, 2018, 10 pages.

(Continued)

*Primary Examiner* — Oneal R Mistry
(74) *Attorney, Agent, or Firm* — Hanley, Flight & Zimmerman, LLC

(57) ABSTRACT

The invention discloses a method and a device for identifying pathological pictures, wherein the method comprises: obtaining sample data including a positive sample that is a pathological picture of malignant lesion and a negative sample that is a picture of normal tissue or a pathological picture of benign lesion, with a lesion area marked on the pathological picture of a malignant lesion; dividing the sample data into a training set and a testing set; training a deep neural network model using the training set; testing a trained deep neural network model using the testing set; adjusting parameters of the trained deep neural network model according to a testing result; identifying the pathological picture using the trained deep neural network model. The invention can improve the efficiency and accuracy of pathological picture identification.

15 Claims, 3 Drawing Sheets

(51) Int. Cl.
   *G16H 50/70* (2018.01)
   *G16H 50/20* (2018.01)
   *G16H 30/40* (2018.01)
   *G06K 9/62* (2006.01)
   *G06N 3/08* (2006.01)

(52) U.S. Cl.
   CPC ........... *G06T 7/0014* (2013.01); *G16H 30/40* (2018.01); *G16H 50/20* (2018.01); *G16H 50/70* (2018.01); *G06T 2207/20081* (2013.01); *G06T 2207/20084* (2013.01); *G06T 2207/30024* (2013.01); *G06T 2207/30096* (2013.01)

(56) References Cited

U.S. PATENT DOCUMENTS

| | | | |
|---|---|---|---|
| 2019/0222817 A1* | 7/2019 | Abou Shousha | G06K 9/0061 |
| 2019/0295252 A1* | 9/2019 | Fuchs | G06N 20/00 |
| 2019/0384047 A1* | 12/2019 | Johnson | G06K 9/3233 |
| 2020/0090039 A1* | 3/2020 | Song | G06N 3/08 |
| 2020/0129263 A1* | 4/2020 | Izadyyazdanabadi | G06K 9/00134 |

FOREIGN PATENT DOCUMENTS

| | | |
|---|---|---|
| CN | 107784319 | 3/2018 |
| CN | 107886127 | 4/2018 |

OTHER PUBLICATIONS

China National Intellectual Property Administration, Search Report issued in connection with Chinese Application No. 201810315279.0, with English translation, dated Nov. 28, 2018, 4 pages.

European Patent Office, Extended European Search Report issued in connection with European Patent Application No. 19168004.0 dated Aug. 14, 2019, 9 pages.

Ghazvinian Zanjani, Farhao et al., "Cancer Detection in Histopathology Whole-Slide Images using Conditional Random Fields on Deep Embedded Spaces", Progress in Biomeoical Optics and Imaging, SPIE—International Society for Optical Engineering, vol. 10581, Mar. 6, 2018, pp. 105810I-105810I, XP60104326, 8 pages.

Sachdev, Jayant et al., "Melanoma Screening Using Deep Neural Networks", 2018 3rd International Conference for Convergence in Technology (I2CT), IEEE, Apr. 6, 2018, pp. 1-5, XP33444087, 6 pages.

Graham, Simon et al., "Classification of Lung Cancer Histology Images using Patch-Level Summary Statistics", Progress in Biomeoical Optics and Imaging, SPIE—International Society for Optical Engineering, vol. 10581, Mar. 6, 2018, pp. 1058119-1058119, XP60104334, 8 pages.

* cited by examiner

METHOD AND DEVICE FOR IDENTIFYING PATHOLOGICAL PICTURE

This application claims priority to Chinese Patent Application No. 201810315279.0, filed on Apr. 10, 2018 and entitled "METHOD AND DEVICE FOR IDENTIFYING PATHOLOGICAL PICTURE", which is incorporated herein by reference in its entirety.

TECHNICAL FIELD

The invention relates to the field of medical technology, in particular to a method and a device for identifying a pathological picture.

BACKGROUND

At present, the pathologist needs to identify and judge the biopsy tissue suspected of nasopharyngeal tumor, to determine whether it is neoplastic, normal or inflammatory; malignant or benign; nasopharyngeal carcinoma or other lesions? Pixel numbers of the length and the width of a pathological picture are both tens of thousands. In order to identify the pathological picture, an expert with extensive experience in nasopharyngeal cancer is generally required to make a careful observation. Not only the whole process is time-consuming, labor-consuming, and experience-depending, with a not very ideal accuracy achieved, but also there may be a risk that doctors with different experiences make different identification conclusions on a same pathological picture.

SUMMARY OF THE INVENTION

Embodiments of the invention provide a method for identifying a pathological picture to improve the efficiency and accuracy of pathological pictures identification, the method comprising:

obtaining sample data including a positive sample that is a pathological picture of a malignant lesion and a negative sample that is a picture of normal tissue or a pathological picture of benign lesion, with a lesion area marked on the pathological picture of a malignant lesion;

dividing the sample data into a training set and a testing set;

training a deep neural network model using the training set;

testing a trained deep neural network model using the testing set;

adjusting parameters of the trained deep neural network model according to a testing result;

identifying the pathological picture using the trained deep neural network model.

Embodiments of the invention also provide a computer device comprising a memory, a processor and a computer program stored on the memory and executable on the processor, when executing the computer program, the processor implementing the following method of:

obtaining sample data including a positive sample that is a pathological picture of a malignant lesion and a negative sample that is a picture of normal tissue or a pathological picture of benign lesion, with a lesion area marked on the pathological picture of a malignant lesion;

dividing the sample data into a training set and a testing set;

training deep neural network model using the training set;

testing a trained deep neural network model using the testing set;

adjusting parameters of the trained deep neural network model according to a testing result;

identifying the pathological picture using the trained deep neural network model.

Embodiments of the invention also provide a computer device which contain storage medium and processor, on which a computer program executing the following method is stored:

obtaining sample data including a positive sample that is a pathological picture of a malignant lesion and a negative sample that is a picture of normal tissue or a pathological picture of benign lesion, with a lesion area marked on the pathological picture of a malignant lesion;

dividing the sample data into a training set and a testing set;

training a deep neural network model using the training set;

testing a trained deep neural network model using the testing set;

adjusting parameters of the trained deep neural network model according to a testing result;

identifying the pathological picture using the trained deep neural network model.

In the embodiments of the invention, firstly sample data is obtained, wherein a pathological picture of a malignant lesion on which a lesion area is marked is taken as a positive sample, a picture of normal tissue or a pathological picture of benign lesion is taken as a negative sample; the sample data is divided into a training set and a testing set; a deep neural network model is trained using the training set; a trained deep neural network model is tested using the testing set; then parameters of the trained deep neural network model are adjusted according to a testing result; thus the trained deep neural network model has a function of automatically identifying a pathological picture, by which an area on a pathological picture that probably contains a malignant lesion can be identified by inputting the pathological picture into the deep neural network model, thereby realizing classification of the pathological picture into a benign or a malignant. The whole process is time-saving and labor-saving, which not only improves the efficiency of pathological picture identification, but also does not depend on personal experience of a doctor, and greatly improves the accuracy of pathological picture identification.

The embodiments of the present invention can be applied not only to identification of a pathological picture of nasopharyngeal carcinoma, but also to identification of a pathological picture of other cancers.

BRIEF DESCRIPTION OF THE DRAWINGS

In order to more clearly explain the embodiments of the invention or the technical solution in the prior art, drawings that need to be used in the description in embodiments or the prior art will be simply introduced below, obviously the drawings in the following description are merely some examples of the invention, for persons ordinarily skilled in the art, it is also possible to obtain other drawings according to these drawings without making creative efforts. In the drawings.

DETAILED DESCRIPTION OF THE EMBODIMENTS

Figure 1:
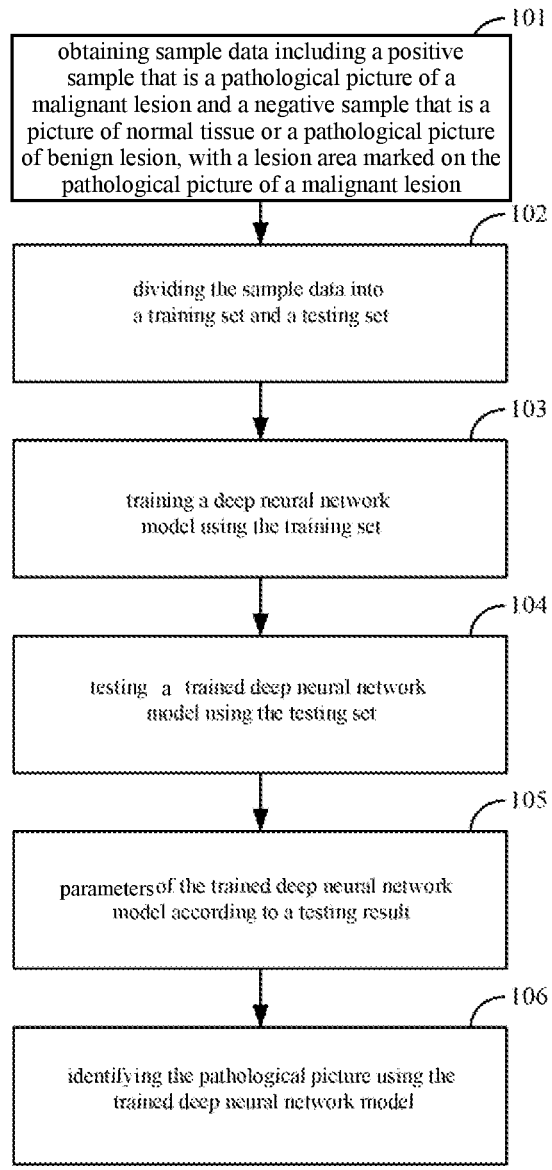
FIG. 1 is the schematic diagram of a method for identifying a pathological picture according to embodiments of the invention.

In order to more clearly explain purpose, technical solution and advantages of embodiments of the invention, hereinafter the embodiments of the invention will be further described in detail in combination with the drawings. Here in the text, the schematic embodiments of the invention and the description thereof are used for explaining the invention and do not constitute definition to the invention.

Technical terms referred to in the embodiments of the invention will be briefly described below.

Accuracy:Accuracy=(number of samples correctly predicted)/(a total number of samples).

Precision:Precision=(number of samples predicted to be 1and correctly predicted)/(all number of samples predicted to be 1).

Recall:Recall=(number of samples predicted to be 1and correctly predicted)/(number of samples that is 1 in all real cases).

Top5 error rate: Usually there are 1000 possible categories of imagenet images, and 5 category labels can be predicted simultaneously for each image. The result of prediction is regarded as correct when any one prediction is correct, and is regarded as wrong only when 5 predictions are all wrong, at this time the classification error rate is called top5 error rate.

Transfer learning: transferring a trained model parameter to a new model to help the new model train the data.

As described above, at present, the technique for identifying whether nasopharyngeal tumor is benign or malignant is mainly a traditional manual classification technique, which requires an experienced professional doctor to carefully observe and make identification on a pathological picture of a gigabit level, and an identification error rate is high. The whole process is time-consuming, labor-consuming and low in accuracy, and there is a risk that doctors with different experiences make different identification conclusions on a same pathological picture. In order to solve this problem, the inventor found in the process of implementing the invention that:

Nowadays, the deep learning technology affects every aspect of the current society, and it has been possible to apply the corresponding technology of artificial intelligence to medical aspects. Although there are not many applications of a deep neural network in medical image processing, significant results have been achieved in image classification by using the deep neural network. GoogLeNet won the championship at the 2014 ILSVRC Challenge, by reducing the top5 error rate to 6.67%. At the 2016 ImageNet Picture Classification Competition, the error rate of the deep neural network for picture classification is only 3.57%, which is lower than 5.1% that is the error rate of a human level, and this indicates that the deep learning technology is feasible in the picture classification, and has a very large advantage. On the basis of GoogLeNet, the network thereof is further improved to form models, namely Inception v1, Inception v2, Inception v3 and Inception v4. These models all can be used for reference in image classification and can be used for transfer learning.

Moreover, in recent years, with the increase of data, improvement of algorithms and enhancement of computing ability, the training depth of artificial neural network has been greatly increased, performance of the artificial neural network has also been greatly improved, and even some aspects have exceeded the human beings. A neural network with multiple hidden layers is called a deep neural network, which makes end-to-end learning become possible without the need of features designed manually. It is time-consuming and labor-consuming, and also requires professional knowledge on this design. Sometimes human cognition may instead limit the performance of the neural network. Instead, the pathological pictures that need to be predicted are input directly to the input layer of the deep neural network, which then automatically outputs the results of benign and malignant classification through learning training. The deep neural network contains multiple hidden layers, these hidden layers can be regarded as multi-layer perception each of which can automatically acquire features of a picture in the training process. A superficial neural network obtains picture features that are local, and a profound neural network can combine the low-level features obtained by the superficial neural network, and then learns higher-level and more abstract features. Finally, the purpose of identifying benign and malignant pictures, i.e., classifying original pictures, is achieved according to these abstract picture features.

Based on this, the inventor considers that in the embodiments of the invention, an expert marks a lesion area on a pathological picture provided by a hospital, and a deep neural network model is trained using these marked data so as to have a function of benign and malignant classification. After that, the pathological picture of a patient is input to the trained model, and then the model can predict the areas on the whole pathological picture that probably have malignant lesions, and make benign and malignant identification. The experimental results show that the accuracy of the model is 98.6%, the precision is 99.1%, and the recall is 98.4%. In the embodiments of the invention, the deep neural network model is used to solve the problems occurring in manual inspection of the pathological specimen, and can provide high reliability.

FIG. 1 is a schematic diagram of a method for identifying a pathological picture according to embodiments of the invention. As shown in FIG. 1, the method may comprise:

a step 101: obtaining sample data including a positive sample that is a pathological picture of a malignant lesion and a negative sample that is a picture of normal tissue or a pathological picture of benign lesion, with a lesion area marked on the pathological picture of a malignant lesion;

a step 102: dividing the sample data into a training set and a testing set;

a step 103: training a deep neural network model using the training set;

a step 104: testing a trained deep neural network model using the testing set;

a step 105: adjusting parameters of the trained deep neural network model according to a testing result;

a step 106: identifying the pathological picture using the trained deep neural network model.

As can be seen from the flow shown in FIG. 1, in the embodiments of the invention, a deep neural network model can be used to automatically identify a pathological picture. An area on the pathological picture that probably has a malignant lesion can be identified by inputting the pathological picture into the deep neural network model, thereby realizing classification of a benign lesion area or a malignant lesion area on the pathological picture. The whole process is time-saving and labor-saving, which not only improves the efficiency of pathological picture identification, but also does not depend on personal experience of the doctor, and greatly improves the accuracy of pathological picture identification. The embodiments of the present invention can be applied not only to identification of pathological pictures of nasopharyngeal carcinoma, but also to identification of pathological pictures of other cancers, such as lung cancer, liver cancer and the like.

In the embodiments, firstly sample data is obtained, the sample data includes a positive sample that is a pathological picture of a malignant lesion and a negative sample that is a picture of normal tissue or a pathological picture of benign lesion, a lesion area is marked on the pathological picture of a malignant lesion. Taking identification of pathological pictures of nasopharyngeal carcinoma as an example, in the embodiments, according to a retrospective clinical research method, a biopsy pathological section of nasopharyngeal carcinoma of a patient that was obtained from a pathology department of a hospital at an earlier stage is firstly scanned by a Leica digital pathology scanner as a 40 times full-field digital pathological picture to be stored in a format of sys. A piece of picture is of gigabit in size, pixel numbers of length and width of the picture can reach tens of thousands. This picture can be previewed with Leica's ImageScope software by a professional pathologist so as to mark the lesion area thereon. After the marking, an xml-formatted label file will be generated.

Since the acquired raw data is so enormous that efficiency may be affected if the raw data is put in the deep neural network model for training, in the embodiments a pre-processing operation may be performed to cut the raw data into ones of suitable size. In particular, after the sample data is obtained, the sample data may further be pre-processed in such a manner that pictures of different dimensions are cut out on the lesion area marked on the pathological picture of a malignant lesion, and pictures of different dimensions are randomly cut on the picture of normal tissue or a pathological picture of benign lesion, in which a picture with cell content less than 50% being discarded, i.e., a sample is regarded as being invalid if an effective tissue region of the sample occupies less than half of the area of the sample. The pictures of different dimensions may include, for example, three pictures of different dimensions, namely 256×256 pixels, 512×512 pixels, and 1024×1024 pixels. Of course, these three dimensions are merely examples, and those skilled in the art can understand that other specific dimensions can also be adopted in the embodiments, which will not be listed in detail herein, and relevant variations should fall within the scope of the invention.

Hereinafter a specific example of pre-processing is given by still taking identification of pathological pictures of nasopharyngeal carcinoma as an example.

In this example, a positive sample indicates that a nasopharynx specimen is a malignant lesion and contains an xml-formatted label file. For such a sample, firstly a labeled area of an original image is recorded, and small pictures of the three dimensions, namely 256×256 pixels, 512×512 pixels, and 1024×1024 pixels, are cut inside the labeled area. This process is repeated until the labeled area on one pathological picture is completely cut. This process is repeated for each pathological picture.

In this example, a negative sample indicates that a nasopharynx specimen is a benign lesion and does not contain an xml-formatted label file. For such a sample, firstly an original image is transformed into a binary image by threshold segmentation, where 0 represents absence of cells and 1 represents presence of cells, and a point being 1 in the binary image is randomly selected as a center point for cutting the image, to cut out small pictures of the three dimensions, namely 256×256 pixels, 512×512 pixels, and 1024×1024 pixels. A picture is discarded if its cell content less than half, and this process is repeated until 1000 small pictures of different dimensions are respectively cut on one pathological picture. This process is repeated for each pathological picture.

In this way, small pictures of positive and negative samples that have different dimensions are obtained, and these pictures can be input to the deep neural network model for training and testing.

After the sample data is obtained, the sample data is divided into a training set and a testing set. For example, for the small pictures of the positive and negative samples as described above, 70% of them are classified into one category as a training set for the purpose of training the deep neural network model, and the remaining 30% of the small pictures are classified into another category as a testing set for the purpose of testing classification performance of the deep neural network model.

Next, the deep neural network model is trained using the training set. At present, there are many mature deep neural network frameworks on the Internet which all have a good picture classification effect, and there is also a full set of weight parameter of the deep neural network that has been trained by others, and the weight parameters can be downloaded directly. This greatly reduces the time required to train the network based on the principle of transfer learning. In order to speed up the training, in the embodiments the deep neural network model can be selected as an Inception v3 after many times of testing. In the training process of the model, model weights and bias are initialized, number of iteration, batch size, convolution kernel size and other parameters are provided and are optimized continuously according to a training result. It can be understood by those skilled in the art that the above described Inception v3 selected as the deep neural network model for pre-training is only an example, and other deep neural network models may be selected during implementation, such as Inception v1, Inception v2, Inception v4 and other models, which will not be listed in detail herein, and relevant variations should fall within the scope of the invention.

In the embodiments, training the deep neural network model using the training set may comprise deploying the training of the deep neural network model onto a plurality of graphics processing units (GPU) to perform a distributed training. For example, based on the distributed training principle of Tensorflow, the training of the model can be deployed on a plurality of GPUs to perform a distributed training, which greatly shortens training time of the model and speeds up the model convergence.

In the embodiments, training the deep neural network model using the training set may comprise inputting pictures of different dimensions respectively to the deep neural network model for training. For example, the data in the training set has small pictures of the three dimensions, namely 256×256 pixels, 512×512 pixels, and 1024×1024 pixels, which are respectively put into the deep neural network model for training, such that the small pictures learn not only texture features of local details, but also structure information of a relatively large entirety, and this can improve the accuracy of the model.

After the deep neural network model is trained by the training set, the trained deep neural network model can be tested using a testing set, that is, the classification performance of the deep neural network model is tested. In the embodiments, testing a trained deep neural network model using the testing set may comprise comparing an identification result of a testing picture with a lesion area label on the testing picture and outputting a testing result. For example, the testing set is sent into the deep neural network model which will identify each small picture, i.e. whether a nasopharyngeal lesion is nasopharyngeal carcinoma or not, a result of which is compared with labels on the picture itself, and then classification accuracy of the deep neural network model can be obtained.

In order to obtain more accurate result, parameters of the trained deep neural network model are adjusted according to the testing result after it is obtained. In the embodiments, when the testing result is incorrect, the testing picture can be mapped back to the original pathological picture, a plurality of pictures having a same dimension are cut around the testing picture, and the cut pictures are input to the deep neural network model for iterative training. For example, a small picture whose classification result is incorrect is mapped back to the original pathological picture where it was located, and then a plurality of small pictures having a same dimension are cut around the small picture, and these data are sent into the deep neural network model for iterative training. The model is fine-tuned to lower as possible probability of misclassification of such small pictures and improve prediction accuracy of the model.

As described above, we use the existing label data to train a deep learning system to help us directly classify and identify benign and malignant pathological pictures. The whole process is time-saving and labor-saving and highly accurate. The experimental results show that the model can finally achieve the accuracy of 98.6%, the precision of 99.1% and the recall of 98.4% after many times of parameter adjusting, training and optimization.

Figure 2:
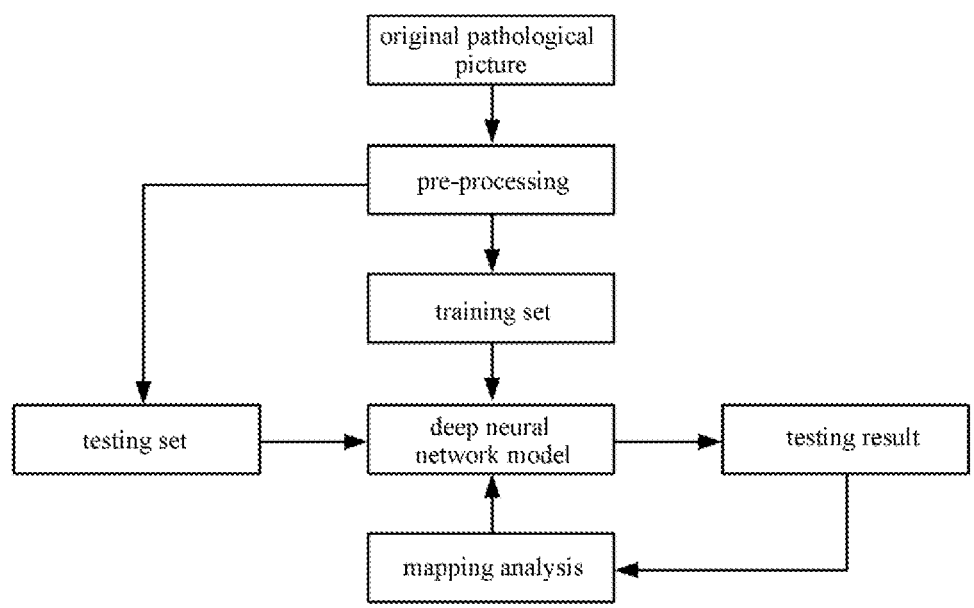
FIG. 2 is the diagram illustrating a specific example of a method for identifying a pathological picture according to the embodiments of the invention.

FIG. 2 is a diagram illustrating a specific example of a method for identifying a pathological picture according to the embodiments of the invention. As shown in FIG. 2, in this example, the original pathological picture is pre-processed, and the pre-processed pathological picture is divided into a training set and a testing set, wherein the training set is input to the deep neural network model for training, and the testing set is input to the trained deep neural network model for testing. After a testing result is obtained, a picture used for testing is mapped back to the original pathological picture for analysis, and then parameters of the deep neural network model are adjusted, thereby a deep neural network model having a function of automatically identifying the pathological picture and classifying into benign and malignant ones with high accuracy is finally obtained.

Figure 3:
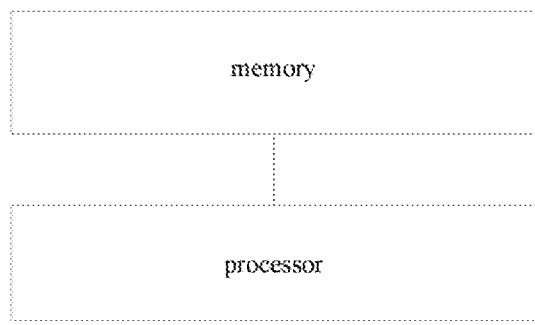
FIG. 3 is the structural diagram of a computer device according to the embodiments of the invention.

Based on same inventive concept, embodiments of the invention also provide a computer device comprising a memory, a processor and a computer program stored on the memory and executable on the processor, as shown in FIG. 3, when executing the computer program, the processor implementing the following method of:

obtaining sample data including a positive sample that is a pathological picture of a malignant lesion and a negative sample that is a picture of normal tissue or a pathological picture of benign lesion, with a lesion area marked on the pathological picture of a malignant lesion;

dividing the sample data into a training set and a testing set;

training a deep neural network model using the training set;

testing a trained deep neural network model using the testing set;

adjusting parameters of the trained deep neural network model according to a testing result; and identifying the pathological picture using the trained deep neural network model.

In one embodiment, after the sample data is obtained, the sample data is further pre-processed by:

cutting out pictures of different dimensions on the lesion area marked on a pathological picture of a malignant lesion; and randomly cutting out pictures of different dimensions on a picture of normal tissue or a pathological picture of benign lesion, and a picture with cell content less than 50% being discarded.

In one embodiment, the pictures of different dimensions include three pictures of different dimensions, namely 256× 256 pixels, 512×512 pixels, and 1024×1024 pixels.

In one embodiment, training the deep neural network model using the training set comprises inputting pictures of different dimensions respectively to the deep neural network model for training;

testing a trained deep neural network model using the testing set comprises comparing an identification result of a testing picture with a lesion area label on the testing picture and outputting a testing result; and adjusting parameters of the trained deep neural network model according to a testing result comprises:

when the testing result is incorrect, mapping the testing picture back to the original pathological picture, cutting out a plurality of pictures having a same dimension around the testing picture, and inputting the cut pictures to the deep neural network model for iterative training.

In one embodiment, the deep neural network model is an Inception v3.

In one embodiment, training the deep neural network model using the training set comprises deploying the training of the deep neural network model onto a plurality of graphics processing units to perform a distributed training.

Embodiments of the invention also provide a computer-readable storage medium, on which a computer program executing the following method is stored:

obtaining sample data including a positive sample that is a pathological picture of a malignant lesion and a negative sample that is a picture of normal tissue or a pathological picture of benign lesion, with a lesion area marked on the pathological picture of a malignant lesion;

dividing the sample data into a training set and a testing set;

training a deep neural network model using the training set;

testing a trained deep neural network model using the testing set;

adjusting parameters of the trained deep neural network model according to a testing result; and identifying the pathological picture using the trained deep neural network model.

In one embodiment, after the sample data is obtained, the sample data is further pre-processed by:

cutting out pictures of different dimensions on the lesion area marked on a pathological picture of a malignant lesion;

randomly cutting out pictures of different dimensions on a picture of normal tissue or a pathological picture of benign lesion, and a picture with cell content less than 50% being discarded.

In one embodiment, the pictures of different dimensions include three pictures of different dimensions, namely 256× 256 pixels, 512×512 pixels, and 1024×1024 pixels.

In one embodiment, training the deep neural network model using the training set comprises inputting pictures of different dimensions respectively to the deep neural network model for training;

testing a trained deep neural network model using the testing set comprises comparing an identification result of a testing picture with a lesion area label on the testing picture and outputting a testing result;

adjusting parameters of the trained deep neural network model according to a testing result comprises:

when the testing result is incorrect, mapping the testing picture back to the original pathological picture, cutting out a plurality of pictures having a same dimension around the testing picture, and inputting the cut pictures to the deep neural network model for iterative training.

In one embodiment, the deep neural network model is an Inception v3.

In one embodiment, training the deep neural network model using the training set comprises deploying the training of the deep neural network model onto a plurality of graphics processing units to perform a distributed training.

From the above, nowadays artificial intelligence technology rises again, and with development of big data, new algorithm and cloud computing, it has been possible to train a deep neural network model, artificial intelligence will have a far-reaching influence on all industries, of course comprises artificial intelligence+medical treatment. In the embodiments of the invention, the advantage of artificial intelligence in picture classification is utilized, and combing the traditional medical treatment, the pathological pictures can be correctly classified.

In the embodiments of the invention, firstly sample data is obtained, wherein a pathological picture of a malignant lesion on which a lesion area is marked is taken as a positive sample, a picture of normal tissue or a pathological picture of benign lesion is taken as a negative sample, the sample data is divided into a training set and a testing set, a deep neural network model is trained using the training set, a trained deep neural network model is tested using the testing set, then parameters of the trained deep neural network model are adjusted according to a testing result, thus the trained deep neural network model has a function of automatically identifying a pathological picture, by which an area on the pathological picture that probably has a malignant lesion can be identified by inputting the pathological picture into the deep neural network model, thereby realizing classification of the pathological picture into those with a benign lesion or those with a malignant lesion. The whole process is time-saving and labor-saving, which not only improves the efficiency of pathological picture identification, but also does not depend on personal experience of the doctor, and greatly improves the accuracy of pathological picture identification, and thus can meet the needs of practical applications.

The embodiments of the present invention can be applied not only to identification of pathological pictures of nasopharyngeal carcinoma, but also to identification of pathological pictures of other cancers.

Persons skilled in the art shall understand that, the embodiments of the present invention can be provided as a method, a system or a computer program product. Therefore, the present invention can adopt the forms of a full hardware example, a full software example, or combination of a software example and a hardware example. Moreover, the present invention can adopt the form of a computer program product that is implemented on one or more computer-usable storage medium (including but not limited to a disk memory, a CD-ROM, an optical memory, and etc.) including computer-usable program codes.

The invention is described with reference to flow diagrams and/or block diagrams of the method, the device (system) and the computer program product according to the embodiment of the invention. It should be understood that each flow and/or block in the flow diagrams and/or block diagrams, and the combination of the flows and/or blocks in the flow diagrams and/or block diagrams can be achieved by computer program instruction. These computer program instruction can be provided to a CPU of a general-purpose computer, a special-purpose computer, an embedded processor or other programmable data processing device to produce a machine, so that a device for achieving functions designated in one or more flows in the flow diagrams and/or one or more blocks in the block diagrams can be generated by the command executed by the CPU of the computer or other programmable data processing device.

These computer program instruction can also be stored in a computer-readable memory that can guide a computer or other programmable data processing device to operate in a special way, so that the command stored in the computer-readable memory generates a manufactured product including a command device which achieves functions designated in one or more flows in the flow diagrams and/or one or more blocks in the block diagrams.

These computer program instruction can also be loaded on a computer or other programmable data processing device, on which a series of operation steps are executed to generate processing achieved by the computer, so that the command executed on the computer or other programmable data processing device is provided for being used in the steps of achieving functions designated in one or more flows in the flow diagrams and/or one or more blocks in the block diagrams.

The purpose, technical solution and beneficial effect of the invention have been further described in detail in the above specific embodiments, it should be understood that the above contents are merely specific embodiments of the invention and are not for limiting protection scope of the invention, and any modifications, equivalent replacements, improvements and the like within the spirit and principle of the present invention shall be included within the protection scope of the present invention.

The invention claimed is:

1. A method for identifying a pathological picture, the method comprising:

obtaining sample data including a positive sample and a negative sample, the positive sample is a pathological picture of a malignant lesion, the negative sample is a picture of normal tissue or a pathological picture of a benign lesion, the positive sample includes a lesion area marked on the pathological picture of the malignant lesion;

preprocessing the sample data by:

cutting out pictures of different dimensions on the lesion area marked on the pathological picture of the malignant lesion; and randomly cutting out pictures of different dimensions on the picture of the normal tissue or the pathological picture of the benign lesion;

dividing the sample data into a training set and a testing set;

training a deep neural network model using the training set to generate a trained deep neural network model, wherein the training of the deep neural network model using the training set includes inputting the pictures of the different dimensions to the deep neural network model;

testing the trained deep neural network model using the testing set by comparing an identification result of a testing picture with a lesion area label on the testing picture and outputting a testing result;

adjusting parameters of the trained deep neural network model according to a testing result, the adjusting of the parameters of the trained deep neural network model according to the testing result including: when the testing result is incorrect, mapping the testing picture back to the original pathological picture, cutting out a plurality of pictures having a same dimension around the testing picture, and inputting the cut pictures to the deep neural network model for iterative training;

identifying the pathological picture using the trained deep neural network model.

2. The method according to claim 1, further comprising: after the pictures of the different dimensions on the picture of normal tissue or the pathological picture of the benign lesion are randomly cut out, discarding.

3. The method according to claim 1, wherein the pictures of different dimensions include three pictures of different dimensions, namely 256×256 pixels, 512×512 pixels, and 1024×1024 pixels.

4. The method according to claim 1, wherein the deep neural network model is an Inception v3 model.

5. The method according to claim 1, wherein the training of the deep neural network model using the training set comprises deploying the training of the deep neural network model onto a plurality of graphics processing units to perform a distributed training.

6. A computer device comprising:
a memory including a computer program, and
a processor a to execute the computer program to:
obtain sample data including a positive sample and a negative sample, the positive sample is a pathological picture of a malignant lesion, the negative sample is a picture of normal tissue or a pathological picture of a benign lesion, the positive sample includes a lesion area marked on the pathological picture of the malignant lesion;
pre-process the sample data by:
cut out pictures of different dimensions on the lesion area marked on the pathological picture of the malignant lesion; and
randomly cut out pictures of different dimensions on the picture of the normal tissue or the pathological picture of the benign lesion;
divide the sample data into a training set and a testing set;
train a deep neural network model using the training set to generate a trained deep neural network model by inputting the pictures of the different dimensions respectively to the deep neural network model;
test the trained deep neural network model using the testing set by comparing an identification result of a testing picture with a lesion area label on the testing picture and outputting a testing result;
adjust parameters of the trained deep neural network model according to the testing result by: when the testing result is incorrect, mapping the testing picture back to the original pathological picture, cutting out a plurality of pictures having a same dimension around the testing picture, and inputting the cut pictures to the deep neural network model for iterative training;

identify the pathological picture using the trained deep neural network model.

7. The computer device according to claim 6, wherein the processor is to: after the pictures of the different dimensions of the picture of the normal tissue or the pathological picture of the benign lesion are randomly cut out,
discard a picture with cell content less than 50% being discarded.

8. The computer device according to claim 6, wherein the pictures of different dimensions include three pictures of different dimensions, namely 256×256 pixels, 512×512 pixels, and 1024×1024 pixels.

9. The computer device according to claim 6, wherein the deep neural network model is an Inception v3 model.

10. The computer device according to claim 6, wherein the processor is to train the deep neural network model using the training set by distributing the training of the deep neural network model onto a plurality of graphics processing units.

11. A computer-readable storage medium comprising a computer program which, when executed, causes a processor to executing the following method:
obtain sample data, the sample data including a positive sample that is a pathological picture of a malignant lesion with a lesion area marked on the pathological picture of the malignant lesion, the sample data including a negative sample that is a picture of normal tissue or a pathological picture of benign lesion,
pre-process the sample data by:
cutting out pictures of different dimensions on the lesion area marked on the pathological picture of the malignant lesion;
randomly cutting out pictures of different dimensions on the picture of the normal tissue or the pathological picture of the benign lesion;
divide the sample data into a training set and a testing set;
train a deep neural network model using the training set to generate a trained neural network model based on the pictures of the different dimensions;
test the trained deep neural network model using the testing set by comparing an identification result of a testing picture with a lesion area label on the testing picture and outputting a testing result;
adjust parameters of the trained deep neural network model according to the testing result by:
when the testing result is incorrect, mapping the testing picture back to the original pathological picture, cutting out a plurality of pictures having a same dimension around the testing picture, and inputting the cut pictures to the deep neural network model for iterative training; and
identify the pathological picture using the trained deep neural network model.

12. The computer-readable storage medium according to claim 11, wherein the instructions cause the processor to: after the pictures of different dimensions on the picture of normal tissue or a pathological picture of benign lesion are randomly cut out, discard.

13. The computer-readable storage medium according to claim 11, wherein the pictures of different dimensions include three pictures of different dimensions, namely 256×256 pixels, 512×512 pixels, and 1024×1024 pixels.

14. The computer-readable storage medium according to claim 11, wherein the deep neural network model is an Inception v3 model.

15. The computer-readable storage medium according to claim 11, wherein the instructions cause the processor to train, training the deep neural network model using the training set by deploying the training of the deep neural network model onto a plurality of graphics processing units to perform a distributed training.

\* \* \* \* \*

UNITED STATES PATENT AND TRADEMARK OFFICE
CERTIFICATE OF CORRECTION

PATENT NO. : 10,970,842 B2  
APPLICATION NO. : 16/380701  
DATED : April 6, 2021  
INVENTOR(S) : Jing-Ping Yun et al.

Page 1 of 1

It is certified that error appears in the above-identified patent and that said Letters Patent is hereby corrected as shown below:

In the Claims

Claim 2, Column 11, Line 23, after "discarding" add "a picture with cell content less than 50%"

Claim 6, Column 11, Line 37, after "processor" delete "a"

Claim 7, Column 12, Line 7-8, after "less than 50%" delete "being discarded"

Claim 11, Column 12, Line 21, after "processor to" delete "executing the following method"

Claim 12, Column 12, Line 57, after "discard" add "a picture with cell content less than 50%"

Signed and Sealed this  
Seventh Day of September, 2021

Drew Hirshfeld  
*Performing the Functions and Duties of the*  
*Under Secretary of Commerce for Intellectual Property and*  
*Director of the United States Patent and Trademark Office*